(12) United States Patent
Amrein et al.

(10) Patent No.: US 7,547,697 B2
(45) Date of Patent: Jun. 16, 2009

(54) ALKYL-PYRIDAZINE DERIVATIVES AS 11B-HSD1 INHIBITORS

(75) Inventors: Kurt Amrein, Itingen (CH); Daniel Hunziker, Moehlin (CH); Bernd Kuhn, Liestal (CH); Werner Neidhart, Hagenthal-le-Bas (FR); Alexander V. Mayweg, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/824,971

(22) Filed: Jul. 2, 2007

(65) Prior Publication Data

US 2008/0009499 A1 Jan. 10, 2008

(30) Foreign Application Priority Data

Jul. 5, 2006 (EP) .................... 06116596

(51) Int. Cl.
| | |
|---|---|
| *A61K 31/502* | (2006.01) |
| *A61K 31/504* | (2006.01) |
| *A61K 31/5025* | (2006.01) |
| *A61K 31/50* | (2006.01) |
| *C07D 237/08* | (2006.01) |
| *C07D 237/14* | (2006.01) |
| *C07D 237/16* | (2006.01) |
| *C07D 237/28* | (2006.01) |
| *C07D 491/08* | (2006.01) |
| *A61P 3/10* | (2006.01) |
| *A61P 3/04* | (2006.01) |
| *A61P 3/06* | (2006.01) |
| *A61P 9/12* | (2006.01) |
| *C07D 307/12* | (2006.01) |
| *C07C 49/105* | (2006.01) |
| *C07C 49/11* | (2006.01) |
| *C07C 49/115* | (2006.01) |
| *C07C 49/12* | (2006.01) |
| *C07C 49/15* | (2006.01) |

(52) U.S. Cl. .................. 514/247; 514/248; 544/224; 544/234; 544/235; 549/463; 568/327; 568/235; 568/308; 568/374; 568/367; 568/375; 568/377; 568/379

(58) Field of Classification Search .......... 514/247, 514/248; 544/224, 234, 235
See application file for complete search history.

(56) References Cited

FOREIGN PATENT DOCUMENTS

| WO | WO 2004/065351 A | 8/2004 |
|---|---|---|
| WO | WO 2004065351 | * 8/2004 |

OTHER PUBLICATIONS

Incyte Corp., Jun. 2008, American Diabetes Association 68th Scientific Sessions, Phase IIa trial of INCB13739.*
Chapman, et al., Neuro. chem. Res. (2008) 33:624-626.*
Hermanowski-Vosatka, et al., J Exp Med. Aug. 15, 2005; 202(4): 517-527.*
Vicker, et al., J. Steroid Biochem. & Molec. Biol., vol. 104, #3-5, May 2007, pp. 123-129.*
Tomlinson, J.W., Stewart, P.M., vol. 1, No. 2, Dec. 2005 pp. 92-99,, XP009090951.
Huang, J. Chem. Soc., Perkin Trans. 1, 1989, 2397.
Boeckman, J. Am. Chem Soc., 1986, 5549.
Albright, J. Org. Chem., 1965 30, 1107.
Kirschberger, B., Synthesis, 1986, 11, 926.
Joshi, K.C., Heterocycles, 1981, 16, 1545.
Swern, D., Synthesis, 1981, 16165.
Baumgarten, J. Am. Chem. Soc. 1958, 80, 6609.
Corey J., Am. Chem. Soc. 1958, 80, 6609.
Katritzky, J., Org. Chem. 1991, 56, 6917.
Baba, A., Org. Chem. 1997, 62, 8282.

* cited by examiner

*Primary Examiner*—Mark L Berch
*Assistant Examiner*—Cecilia M Jaisle
(74) *Attorney, Agent, or Firm*—George W. Johnston; Dennis P. Tramaloni; Samuel H. Megerditchian

(57) ABSTRACT

Compounds of formula (I):

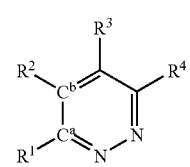

as well as pharmaceutically acceptable salts and esters thereof for use as pharmaceutical compositions.

19 Claims, No Drawings

ALKYL-PYRIDAZINE DERIVATIVES AS 11B-HSD1 INHIBITORS

PRIORITY TO RELATED APPLICATION(S)

This application claims the benefit of European Patent Application No. 06116596.5, filed Jul. 5, 2006, which is hereby incorporated by reference in its entirety.

FIELD OF THE INVENTION

The present invention is concerned with novel pyridazine derivatives useful as 11b-HSD1 inhibitors (T2D).

The invention is concerned preferably with compounds of formula I

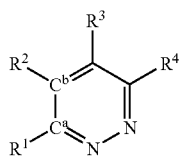

and pharmaceutically acceptable salts and esters thereof.

All documents cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (Cortisol in humans) and their inactive 11-keto metabolites (cortisone in humans).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. Dec. 7, 2001; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in men might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and lack major side effects. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci U.S.A. Dec. 23, 1997;94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. Jul 2003;112(1): 83-90; Rauz S. et al., QJM. Jul 2003;96(7):481-90) to improve cognition (Sandeep T C. et al., Proc Natl Acad Sci USA. Apr. 27, 2004;101(17):6734-9) or to improve Alzheimer associated deficits. Taken together 11beta-HSD1 inhibition might be a safe and efficacious approach to treat symptoms of diabetes, obesity and other diseases.

SUMMARY OF THE INVENTION

In an embodiment of the present invention, provided are compounds of formula (I):

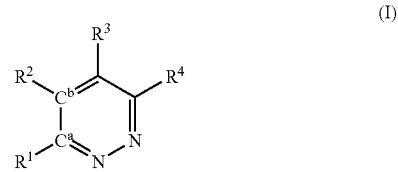

wherein
R¹ is cycloalkyl, arylalkyl or aryloxyalkyl;
R² is cycloalkyl, arylalkyl or aryloxyalkyl; or
R¹ and R² together with the carbon atoms $C^a$ and $C^b$ to which they are attached form

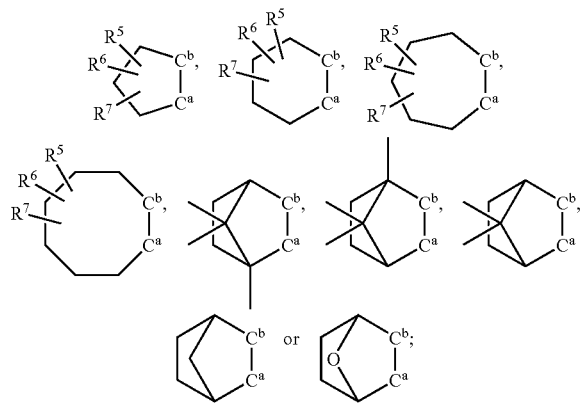

R³ is hydrogen, alkyl, cycloalkyl or trifluoromethyl;
R⁴ is 2,2-dimethyl-propyl, 3-methyl-butyl, iso-propyl, tert-butyl, cyclopropylmethyl, cyclopentylmethyl, 3,3-dimethyl-butyl or 1-cyclopropyl-1-methyl-ethyl;
R⁵ is hydrogen, alkyl, cycloalkyl or alkoxy,
R⁶ is hydrogen, alkyl, cycloalkyl or alkoxy;
R⁷ is hydrogen, alkyl, cycloalkyl or alkoxy;
and pharmaceutically acceptable salts and esters thereof.

In another embodiment of the present invention, provided is a process for the preparation of a compound according to formula (I), comprising the of the step of reacting a compound according to formula (II)

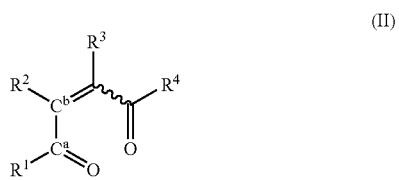

with hydrazine; wherein R¹ to R⁴ are defined as in claim 1.

In a further embodiment of the present invention, provided is a pharmaceutical composition, comprising a therapeutically effective amount of a compound according to formula (I) and a therapeutically inert carrier.

In a still another embodiment of the present invention, provided is a method for the treatment of diabetes, obesity, eating disorders, dyslipidemiae and hypertension, comprising the step of administering a therapeutically effective amount of a compound according to formula (I) to a patient in need thereof.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

Further, the compounds of this invention can be used for promoting wound healing, particularly by topical application. Moreover, the compounds of the present invention can be used to improve cognitive impairment, particularly impairment developed with age, and improvement of memory.

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment or prophylaxis of eating disorders, obesity, dyslipidemiae, hypertension and/or diabetes, particularly diabetes Type II, and the use of the said compounds, salts and esters for the production of medicaments for the treatment or prophylaxis of metabolic disorders, obesity, dyslipidemiae, hypertension and/or diabetes, particularly diabetes Type II.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl are methyl-cyclopropyl and particularly 1-methyl-cyclopropyl. Particularly preferred is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl.

The term "aryloxy", alone or in combination, signifies a aryl-O— group in which the term "aryl" has the previously given significance.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" (C*) means a carbon atom with four different substituents. According to the Cahn-Ingold-Prelog Convention the asymmetric carbon atom can be of the "R" or "S" configuration.

Preferred are the compounds of formula I and pharmaceutically acceptable salts thereof, particularly the compounds of formula I.

Preferred are compounds of formula I, wherein $R^1$ and $R^2$ together with the carbon atoms $C^a$ and $C^b$ to which they are attached form

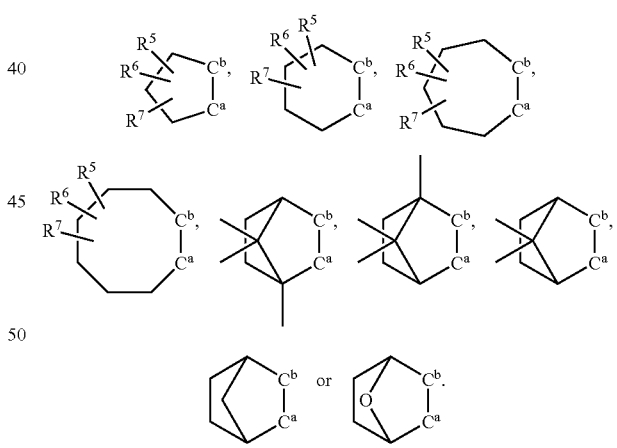

Further preferred are compounds of formula I, wherein $R^1$ and $R^2$ together with the carbon atoms $C^a$ and $C^b$ to which they are attached form

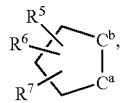

have the following formula

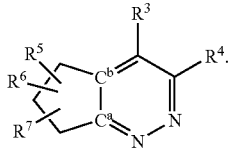
(Ia)

Also preferred are compounds of formula I, wherein $R^1$ and $R^2$ together with the carbon atoms $C^a$ and $C^b$ to which they are attached form

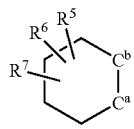

have the following formula

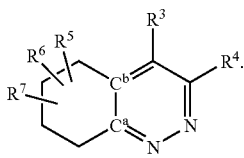
(Ib)

Preferred are compounds of formula I, wherein $R^1$ and $R^2$ together with the carbon atoms $C^a$ and $C^b$ to which they are attached form

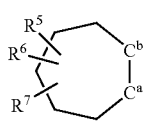

have the following formula

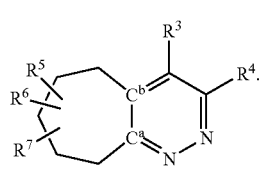
(Ic)

Further preferred are compounds of formula I, wherein $R^1$ and $R^2$ together with the carbon atoms $C^a$ and $C^b$ to which they are attached form

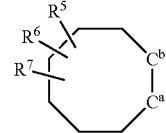

have the following formula

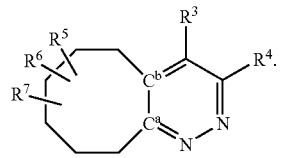
(Id)

Further preferred are compounds of formula I, wherein $R^1$ and $R^2$ together with the carbon atoms $C^a$ and $C^b$ to which they are attached form

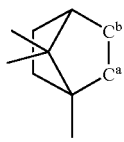

have the following formula

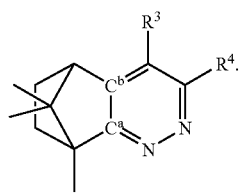
(Ie)

Further preferred are compounds of formula I, wherein $R^1$ and $R^2$ form together with the carbon atoms $C^a$ and $C^b$ to which they are attached

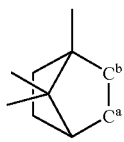

have the following formula

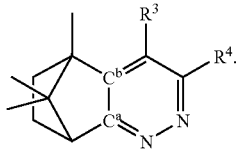
(If)

Further preferred are compounds of formula I, wherein $R^1$ and $R^2$ form together with the carbon atoms $C^a$ and $C^b$ to which they are attached

have the following formula

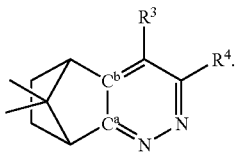
(Ig)

Also preferred are compounds according to formula I, wherein $R^1$ and $R^2$ form together with the carbon atoms $C^a$ and $C^b$ to which they are attached

have the following formula

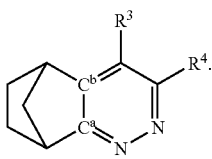
(Ih)

Preferred are compounds of formula I, wherein $R^1$ and $R^2$ form together with the carbon atoms $C^a$ and $C^b$ to which they are attached

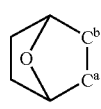

have the following formula

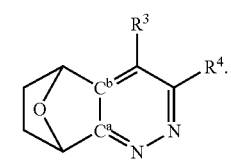
(Ii)

Further preferred are compounds of formula I, wherein $R^1$ and $R^2$ together with the carbon atoms $C^a$ and $C^b$ to which they are attached form

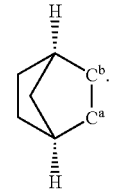

Particularly preferred are those compounds of formula I, wherein $R^1$ and $R^2$ together with the carbon atoms $C^a$ and $C^b$ to which they are attached form

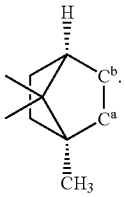

Further particularly preferred are those compounds of formula I, wherein $R^1$ and $R^2$ together with the carbon atoms $C^a$ and $C^b$ to which they are attached form

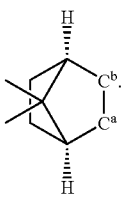

Also particularly preferred are those compounds of formula I, wherein $R^1$ and $R^2$ together with the carbon atoms $C^a$ and $C^b$ to which they are attached form Also particularly preferred are those compounds of formula I, wherein $R^1$ and $R^2$ together with the carbon atoms $C^a$ and $C^b$ to which they are attached form

Further preferred are the compounds of formula I, wherein $R^3$ is hydrogen. Also preferred are the compounds of formula I, wherein $R^3$ is methyl.

Preferred are compounds according to formula I, wherein $R^4$ is 2,2-dimethyl-propyl, 3-methyl-butyl, iso-propyl, tert-butyl, cyclopropylmethyl or cyclopentylmethyl.

Preferred are those compounds of formula I, wherein $R^4$ is 2,2-dimethyl-propyl, 3-methyl-butyl, iso-propyl or tert-butyl. Particularly preferred are the compounds of formula I, wherein $R^4$ is 2,2-dimethyl-propyl or tert-butyl. Further particularly preferred are those compounds of formula I, wherein $R^4$ is 3-methyl-butyl.

A further preferred aspect of the present invention are the compounds of formula I, wherein $R^5$, $R^6$ and $R^7$ are independently selected from hydrogen and methyl. Particularly preferred are those compounds of formula I, wherein $R^5$, $R^6$ and $R^7$ are hydrogen.

Preferred are chiral compounds of formula I.

Preferred are those compounds of formula I, wherein $R^1$ and $R^2$ together with the carbon atoms $C^a$ and $C^b$ to which they are attached form

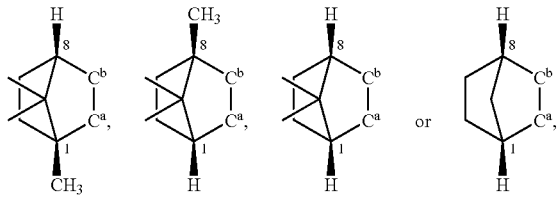

wherein the carbon atom of the 1 position is of the R configuration and the carbon atom of the 8 position is of the S configuration.

Particularly preferred are those compounds of formula I, wherein $R^1$ and $R^2$ together with the carbon atoms $C^a$ and $C^b$ to which they are attached form

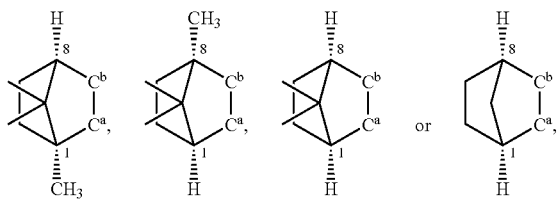

wherein the carbon atom of the 1 position are of the S configuration and the carbon atom of the 8 position is of the R configuration.

Further particularly preferred are those compounds of formula I, wherein $R^1$ and $R^2$ together with the carbon atoms $C^a$ and $C^b$ to which they are attached form

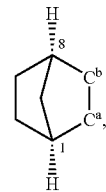

wherein the carbon atom of the 1 position is of the R configuration and the carbon atom of the 8 position is of the S configuration.

Further particularly preferred are the compounds according to formula I, wherein $R^1$ and $R^2$ together with the carbon atoms $C^a$ and $C^b$ to which they are attached form

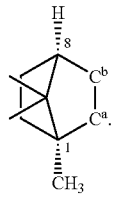

According to the above formula the carbon atom of the 1 position is of the S configuration and the carbon atom of the 8 position is of the R configuration.

Examples of preferred compounds of formula (I) are:
1. 3-(2,2-Dimethyl-propyl)-5,6,7,8,9,10-hexahydro-cycloocta[c]pyridazine;
2. (1SR,8RS)-5-(2,2-Dimethyl-propyl)-3,4-diaza-tricyclo[6.2.1.0$^{2,7}$]undeca-2,4,6,-triene;
3. (1S,8R)-5-(2,2-Dimethyl-propyl)-1,11,11-trimethyl-3,4-diaza-tricyclo[6.2.1.0$^{2,7}$]undeca-2,4,6-triene;
4. (1S,8R)-5-tert-Butyl-1,11,11-trimethyl-3,4-diaza-tricyclo[6.2.1.0$^{2,7}$]undeca-2,4,6-triene;
5. 3-(2,2-Dimethyl-propyl)-6,6-dimethyl-6,7-dihydro-5H-cyclopenta[c]pyridazine;
6. (1SR,8RS)-5-(2,2-Dimethyl-propyl)-6-methyl-3,4-diazatricyclo[6.2.1.0$^{2,7}$]undeca-2,4,6-triene;
7. 3-tert-Butyl-6,6-dimethyl-6,7-dihydro-5H-cyclopenta[c]pyridazine;
8. (1SR,8RS)-5-(3-Methyl-butyl)-3,4-diaza-tricyclo[6.2.1.0$^{2,7}$]undeca-2(7),3,5-triene;
9. (1SR,8RS)-5-tert-Butyl-3,4-diaza-tricyclo[6.2.1.0$^{2,7}$]undeca-2,4,6-triene;
10. (1S,8R)-1,11,11-Trimethyl-5-(3-methyl-butyl)-3,4-diaza-tricyclo[6.2.1.0$^{2,7}$]undeca-2,4,6-triene;
11. (1S,8R)-5-Isopropyl-1,11,11-trimethyl-3,4-diaza-tricyclo[6.2.1.0$^{2,7}$]undeca-2,4,6-triene;
12. (1SR,8RS)-5-Cyclopropylmethyl-3,4-diaza-tricyclo[6.2.1.0$^{2,7}$]undeca-2(7),3,5-triene;
13. (1S,8R)-5-Cyclopropylmethyl-1,11,11-trimethyl-3,4-diaza-tricyclo[6.2.1.0$^{2,7}$]undeca-2(7),3,5-triene;
14. 3-Cyclopropylmethyl-6,6-dimethyl-6,7-dihydro-5H-cyclopenta[c]pyridazine; and
15. (1S,8R)-5-Cyclopentylmethyl-1,11,11-trimethyl-3,4-diaza-tricyclo[6.2.1.0$^{2,7}$]undeca-2,4,6-triene.

Examples of particularly preferred compounds of formula (I) are:
(1SR,8RS)-5-(2,2-Dimethyl-propyl)-3,4-diaza-tricyclo [6.2.1.0$^{2,7}$]undeca-2,4,6-triene;
(1S,8R)-5-(2,2-Dimethyl-propyl)-1,11,11-trimethyl-3,4-diaza-tricyclo[6.2.1.0$^{2,7}$]undeca-2,4,6-triene;
(1S,8R)-5-tert-Butyl-1,11,11-trimethyl-3,4-diaza-tricyclo [6.2.1.0$^{2,7}$]undeca-2,4,6-triene;
(1SR,8RS)-5-(2,2-Dimethyl-propyl)-6-methyl-3,4-diaza-tricyclo[6.2.1.0$^{2,7}$]undeca-2,4,6-triene;
3-tert-Butyl-6,6-dimethyl-6,7-dihydro-5H-cyclopenta[c]pyridazine; and
(1S,8R)-1,11,11-Trimethyl-5-(3-methyl-butyl)-3,4-diaza-tricyclo[6.2.1.0$^{2,7}$]undeca-2,4,6-triene;

Further preferred examples of the present invention are
(1S,8R)-5-(2,2-Dimethyl-propyl)-6-methyl-3,4-diaza-tricyclo[6.2.1.0$^{2,7}$]undeca-2,4,6-triene;
(1S,8R)-5-(2,2-Dimethyl-propyl)-6-methyl-3,4-diaza-tricyclo[6.2.1.0$^{2,7}$]undeca-2,4,6-triene;
(1S,8R)-5-(3,3-Dimethyl-butyl)-1,11,11-trimethyl-3,4-diaza-tricyclo[6.2.1.0$^{2,7}$]undeca-2,4,6-triene;
(1SR,8RS)-5-tert-Butyl-11,11-dimethyl-3,4-diaza-tricyclo [6.2.1.0$^{2,7}$]undeca-2,4,6-triene;
(1S,8R)-5-tert-Butyl-11,11-dimethyl-3,4-diaza-tricyclo [6.2.1.0$^{2,7}$]undeca-2,4,6-triene;
(1R,8S)-5-tert-Butyl-11,11-dimethyl-3,4-diaza-tricyclo [6.2.1.0$^{2,7}$]undeca-2,4,6-triene;
(1SR,8RS)-5-(2,2-Dimethyl-propyl)-11,11-dimethyl-3,4-diaza-tricyclo[6.2.1.0$^{2,7}$]undeca-2,4,6-triene;
(1SR,8RS)-5-(2,2-Dimethyl-propyl)-6,11,11-trimethyl-3,4-diaza-tricyclo[6.2.1.0$^{2,7}$]undeca-2,4,6-triene;
(1SR,8RS)-5-(1-Cyclopropyl-1-methyl-ethyl)-3,4-diaza-tricyclo[6.2.1.0$^{2,7}$]undeca-2,4,6-triene;
(1SR,8RS)-5-Cyclopentylmethyl-3,4-diaza-tricyclo [6.2.1.0$^{2,7}$]undeca-2,4,6-triene;
(1R,8S)-5-(2,2-Dimethyl-propyl)-1,11,11-trimethyl-3,4-diaza-tricyclo[6.2.1.0$^{2,7}$]undeca-2(7),3,5-triene;
(1S,8R)-5-(2,2-Dimethyl-propyl)-8,11,11-trimethyl-3,4-diaza-tricyclo[6.2.1.0$^{2,7}$]undeca-2(7),3,5-triene;
(1R,8S)-5-tert-Butyl-1,11,11-trimethyl-3,4-diaza-tricyclo [6.2.1.0$^{2,7}$]undeca-2(7),3,5-triene; and
(1S,8R)-5-tert-Butyl-8,11,11-trimethyl-3,4-diaza-tricyclo [6.2.1.0$^{2,7}$]undeca-2(7),3,5-triene.

Further examples of particularly preferred compounds of formula (I) are:
(1S,8R)-5-(2,2-Dimethyl-propyl)-6-methyl-3,4-diaza-tricyclo[6.2.1.0$^{2,7}$]undeca-2,4,6-triene;
(1S,8R)-5-(2,2-Dimethyl-propyl)-6-methyl-3,4-diaza-tricyclo[6.2.1.0$^{2,7}$]undeca-2,4,6-triene;
(1S,8R)-5-tert-Butyl-11,11-dimethyl-3,4-diaza-tricyclo [6.2.1.0$^{2,7}$]undeca-2,4,6-triene;
(1R,8S)-5-tert-Butyl-11,11-dimethyl-3,4-diaza-tricyclo [6.2.1.0$^{2,7}$]undeca-2,4,6-triene;
(1SR,8RS)-5-(2,2-Dimethyl-propyl)-11,11-dimethyl-3,4-diaza-tricyclo[6.2.1.0$^{2,7}$]undeca-2,4,6-triene;
(1S,8R)-5-(2,2-Dimethyl-propyl)-8,11,11-trimethyl-3,4-diaza-tricyclo[6.2.1.0$^{2,7}$]undeca-2(7),3,5-triene; and
(1S,8R)-5-tert-Butyl-8,11,11-trimethyl-3,4-diaza-tricyclo [6.2.1.0$^{2,7}$]undeca-2(7),3,5-triene.

Processes for the manufacture of compounds of formula I are an embodiment of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

In general, compounds of type I are readily accessible by treatment of compounds of formula II with hydrazine: different reaction conditions can be used to perform the condensation reaction, e.g.: heating II with hydrazine monohydrate in toluene in the presence of an acid such as p-toluene sulfonic acid, (ii) heating II and hydrazine monohydrate in a mixture of water/acetic acid at reflux temperature, (iii) heating II and hydrazine monohydrate in a mixture of water/acetic acid at reflux temperature which is then followed, after work-up, by a basic treatment with NaOMe in n-butanol at reflux temperature to complete the ring closing reaction to pyridazine. The application of the different conditions depends on the respective starting materials used and is outlined in the experimental part. The geometries of the double bond of compounds of type II can be E or Z, or mixtures of E and Z. Independent of the double bond geometry, they can be converted to I by choosing the most appropriate reaction conditions outlined above, and as exemplified in the experimental part.

In cases were R1 and R2 form 5 to 8 membered rings, the synthesis of these analogues of formula II via a Horner-Wittig reaction (chapter below) can give rise to isomeric compounds, with the double bond migrated into the ring system, and as exemplified in formula IIa for the 7 membered ring system. Also these isomers can be directly converted to II by employing the reaction conditions outlined above.

Scheme 1

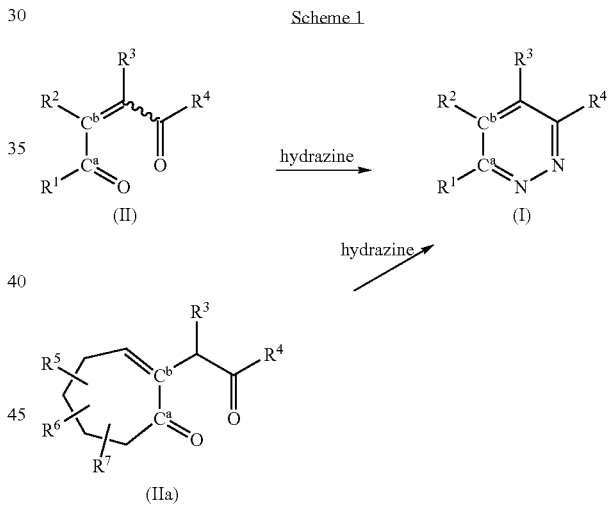

The compound of type II, employed in scheme 1 as starting materials, can be prepared as summarized in scheme 2:

Thus, on reacting a 1,2-diketone of formula III with a phosphonate of formula IV in a Horner-Emmons (or Wittig-Horner) reaction, this gives rise to compounds of formula II. The conditions that can be used are, e.g.: potassium tert-butoxide as a base in tert-butanol as solvent under reflux conditions. Depending on the starting material, double bond migration can occur were possible, as shown in formula IIa for compounds were R1, R2 form a 7 membered ring, and as exemplified in the experimental part.

The double bond geometries of the compounds of formula II can be E, Z or a mixture of E and Z depending on the R1, R2; R3, R4 groups. In many cases only one isomer (the thermodynamically more stable E isomer) is predominantly formed. In cases were mixtures are obtained these can be separated by chromatography or used as mixtures in the ring forming reaction. The stereochemistry of the double bond can be assigned by NMR for the compounds of formula II (experimental part). Instead of a phosphonate of type IV it is also possible to use a corresponding alpha-halo ketone analogue and performing a Reformatsky reaction followed by water elimination (for an example of this type of reaction: Huang, J. Chem. Soc., Perkin Trans. 1, 1989, 2397).

For compounds of formula III that are not symmetric, compounds of formula II are directly obtained in cases where the Cb carbonyl group is more reactive then Ca carbonyl. In cases were the two carbonyl groups can react, mixtures can be obtained, which can be separated by chromatography and processed further accordingly.

In cases were the Ca carbonyl group is the more reactive in regard to the Horner-Emmons (or Wittig-Horner) reaction—compounds of formula II can be obtained via several routes, e.g.: (i) conversion of the Ca carbonyl into a cyclic ketal group on reaction with, for example, ethane-1,2-diol (analogues to: Boeckman, J. Am. Chem. Soc., 1986, 5549), performing the Wittig-Horner reaction at Cb followed by Ca ketal cleavage; or alternatively: (ii) reduction of the Ca carbonyl group to hydroxy and protection, for example, as a t-butyl-dimethyl-silyl ether (for an example: Boeckman, J. Am. Chem. Soc., 1986, 5549), performing then the Horner-Wittig reaction at Cb, de-protection and final oxidation of hydroxy back to carbonyl—using, for example, the Swern oxidation conditions (for an example of the reaction: Albright, J. Org. Chem., 1965 30, 1107).

The phosphonates of formula IV are either known in the literature ore can be prepared by standard procedures. An example of preparing compounds IV includes, for example, treating an alkyl-phosphonic acid dimethyl ester with a base such as N-butyllithium, in THF as solvent at −78° C. and subsequent reaction with an alkyl carboxylate to give IV. Alternatively, methyl-phosphonic acid dimethyl ester (R3=H) can be used in the reaction, with an subsequent alkylation step to introduce R3-reacting IV (R=H) with an alkylating reagent (R3-hal) in the presence of a base such as potassium t-butoxide or N-butyllithium or potassium carbonate (for an analogous reaction: B. Kirschberger, Synthesis, 1986, 11, 926).

Alternative ways to prepare compounds of formula II include reacting a ketone of formula V with compounds of formula VI according to Scheme 3. The reaction can be achieved in analogy to a method described by Mukaiyama (J. Am. Chem. Soc., 1974, 96, 7503) via a cross aldol reaction, reacting V, via its pre-formed silyl enol-ether, with a formyl carbonyl of formula IV, in the presence of titanium tetrachloride, to give II after dehydration of the primary coupling product. Compounds VI are either commercial available ore prepared in analogy to methods described in the literature, e.g. from corresponding methyl ketones and $SeO_2$ oxidation (for a literature example: K. C. Joshi, Heterocycles, 1981, 16, 1545), or from alpha-halo ketones and Swern oxidation (for an example; D. Swern, Synthesis, 1981, 165).

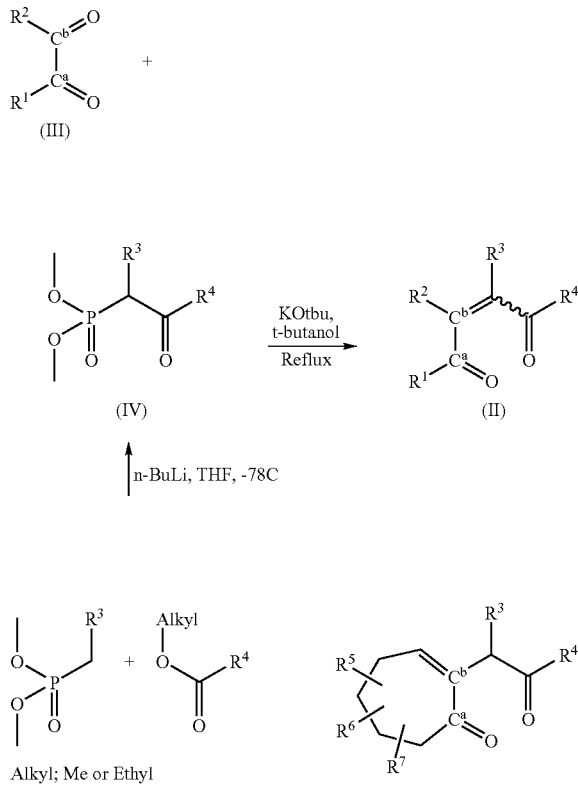

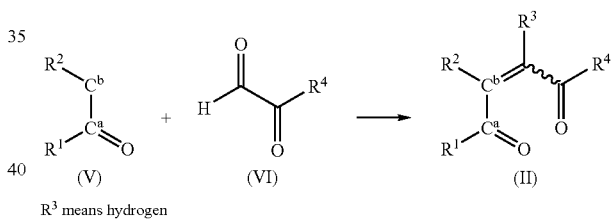

The compounds of formula V are either commercial, described in the literature or can be prepared by applying known procedures.

A further alternative way to prepare compounds of formula I is outlined in scheme 4: reacting 1,4-diketones of formula VII with hydrazine under conditions discussed above to give the dihydropyridazines of formula VIII (one of several possible isomeric forms drawn). These can then be aromatized with, for example, Pd on charcoal or another oxidation reagent such as $Br_2$ (for analogues procedures: Baumgarten, J. Am. Chem. Soc. 1958, 80, 6609) to give compounds of formula I. The 1,4 diketones of formula VII are widely used synthetic building blocks and numerous methods for their preparation are known in the literature (for example: Corey J. Am. Chem. Soc. 1969, 91, 4926; Katritzky, J. Org. Chem. 1991, 56, 6917). A more recent example to prepare these compounds is to use the procedure published by A. Baba (J. Org. Chem, 1997, 62, 8282): reacting ketone V, via prior conversion to the corresponding tin enolate, with the alpha-halo ketone IX in the presence of catalytic amounts of $ZnCl_2$ (Scheme 4).

The 1,2-diketones III used in scheme II are either commercial, known in the literature or can be prepared by combination of methods known in the art.

Scheme 4

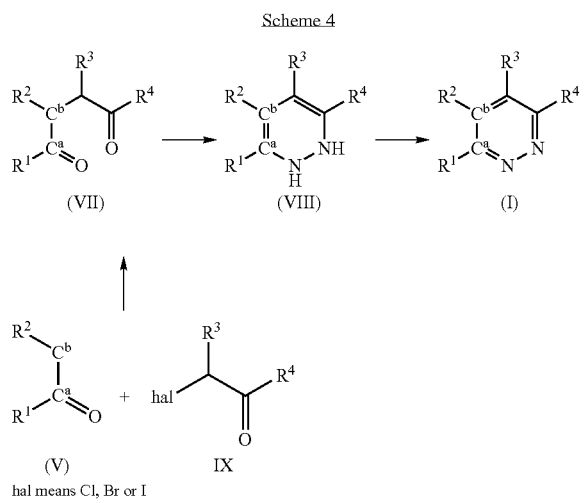

hal means Cl, Br or I

A preferred process for the preparation of a compound of formula

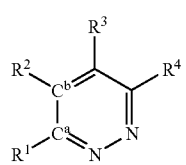
(I)

comprises the reaction of a compound according to formula

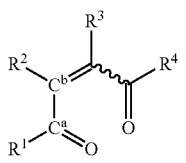
(II)

with hydrazine in order to obtain a compound according to formula I;
wherein $R^1$ to $R^4$ are defined as before.

The compounds of formula I described above for use as therapeutically active substance are a further embodiment of the invention.

Also an embodiment of the present invention are compounds as described above for the preparation of medicaments for the prophylaxis and therapy of illnesses which are caused by disorders associated with the enzyme 11beta-hydroxysteroid dehydrogenase1 (11bHSD1).

Likewise an embodiment of the invention are pharmaceutical compositions comprising a compound of the formula I as described above and a therapeutically inert carrier.

A further preferred embodiment of the present invention is the use of a compound of the formula I as described above for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

A further embodiment of the present invention comprises a compound according to formula I as described above, when manufactured according to any one of the described processes.

Also an embodiment of the invention is a method for the treatment and prophylaxis of diabetes, obesity, eating disorders, dyslipidemiae and hypertension, which method comprises administering an effective amount of a compound of formula I as described above.

Particularly preferred is a method for the treatment and prophylaxis of diabetes Type II, which method comprises administering an effective amount of a compound according to formula I as described above.

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48h after transfection cells were washed twice with ice-cold PBS (Phosphate buffered Saline). To 1 volume of cell suspension in PBS 2 volumes of ice-cold lysis buffer (50 mM Tris; pH 7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

Results obtained in the microsome assay using representative compounds of the invention as the test compounds are shown in the following table:

| Compound | h 11-beta-HSD 1 $IC_{50}$ (nM) |
| --- | --- |
| Example 1 | 6 |
| Example 3 | 14 |

Compounds as described above have $IC_{50}$ values below 1000 nM; preferred compounds have $IC_{50}$ values below 100 nM. More preferred compounds have $IC_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

3-(2,2-Dimethyl-propyl)-5,6,7,8,9,10-hexahydro-cycloocta[c]pyridazine

Step A]: (4,4-Dimethyl-2-oxo-pentyl)-phosphonic acid dimethyl ester

A solution of methyl-phosphonic acid dimethyl ester (9.53 g) in THF (50 mL) under an argon atmosphere was cooled to −65° C. and treated dropwise with 48 mL of a 1.6 M solution of N-butyllithium in hexane keeping the temperature of the reaction mixture below −65° C. After stirring for 15 minutes 3,3-dimethyl-butyric acid methyl ester (5 g in 5 ml THF) were added slowly and the mixture was stirred for 30 minutes (temperature below −65° C.). The reaction mixture was allowed to warm to 0° C., quenched with 1N aqueous HCl, and then partitioned between ACOEt and water. The layers were separated, the organic layer was washed with water, dried over MgSO$_4$, filtered and evaporated to give 4,4-dimethyl-2-oxo-pentyl)-phosphonic acid dimethyl ester (9.21 g) as a light yellow liquid that was used in the next reaction without further purification. MS (ESI): 223.2 (MH$^+$).

Step B]: (Z)-2-(4,4-Dimethyl-2-oxo-pentyl)-cyclooct-2-enone

A solution of potassium tert-butoxide (0.192 g) in tert-butanol (10 mL) under an argon atmosphere was treated at 50° C. with (4,4-dimethyl-2-oxo-pentyl)-phosphonic acid dimethyl ester (0.38 g) and cyclooctane-1,2-dione (0,2 g), and the mixture was then heated at reflux for 12 h under an argon atmosphere. The reaction mixture was partitioned between water and AcOEt, the layers were separated, the aqueous layer extracted twice with AcOEt. The combined organic layers were washed with water, dried over Na$_2$SO$_4$, filtered and evaporated. The residue was purified by flash chromatography (heptane/AcOEt 100% to 95%) to give (Z)-2-(4,4-dimethyl-2-oxo-pentyl)-cyclooct-2-enone (0.076 g) as a light yellow oil. MS (ESI): 237.0 (MH$^+$).

Step C]: 3-(2,2-Dimethyl-propyl)-5,6,7,8,9,10-hexahydro-cycloocta[c]pyridazine (i) A solution of (Z)-2-(4,4-Dimethyl-2-oxo-pentyl)-cyclooct-2-enone (0.07 g) in ethanol (6 ml) was treated at RT with water (1.5 ml), hydrazine monohydrate (0.07 ml) and acetic acid (1.5 ml), and the mixture was then heated to reflux for 12 h (oil bath temperature: 105° C.). The reaction mixture was partitioned between water and AcOEt. The combined organic layers were washed with 2M aqueous $KHCO_3$, dried over $Na_2SO_4$, filtered and evaporated. The residue was purified by flash chromatography (heptane/AcOEt 100% to 85%) to give 3-(2,2-dimethyl-propyl)-5,6,7,8,9,10-hexahydro-cyclooct a[c]pyridazine, (0.018 g) as an amorphous white solid. MS (ESI): 233.2 ($MH^+$).

Further compounds that were prepared according to example 1, steps A] to C]:

Example 2

(1SR,8RS)-5-(2,2-Dimethyl-propyl)-3,4-diaza-tricyclo[6.2.1.0$^{2,7}$]undeca-2,4,6,-triene light-yellow solid. MS (ESI): 217.2 ($MH^+$). Prepared from bicyclo[2.2.1]heptan-2,3-dione, (4,4-dimethyl-2-oxo-pentyl)-phosphonic acid dimethyl ester, hydrazine monohydrate.

Example 3

(1S,8R)-5-(2,2-Dimethyl-propyl)-1,11,11-trimethyl-3,4-diaza-tricyclo[6.2.1.0$^{2,7}$]undeca-2,4,6-triene light-yellow solid. MS (ESI): 258.9 ($MH^+$). Prepared from (1S,4R)-1,7,7-trimethyl-bicyclo[2.2.1]heptane-2,3-dione, (4,4-dimethyl-2-oxo-pentyl)-phosphonic acid dimethyl ester, hydrazine monohydrate.

Example 4

(1S,8R)-5-tert-Butyl-1,11,11-trimethyl-3,4-diaza-tricyclo[6.2.1.0$^{2,7}$]undeca-2,4,6-triene MS (EI): 244.3 ($M^+$), light-yellow crystalline solid. Prepared from (1S,4R)-1,7,7-trimethyl-bicyclo[2.2.1]heptane-2,3-dione, (3,3-dimethyl-2-oxo-butyl)-phosphonic acid dimethyl ester, hydrazine monohydrate.

Example 5

3-(2,2-Dimethyl-propyl)-6,6-dimethyl-6,7-dihydro-5H-cyclopenta[c]pyridazine off-white solid. MS (ESI): 219.3 ($MH^+$). Prepared from 4,4-dimethyl-cyclopentane-1,2-dione, (4,4-dimethyl-2-oxo-pentyl)-phosphonic acid dimethyl ester, hydrazine monohydrate.

Example 6

(1SR,8RS)-5-(2,2-Dimethyl-propyl)-6-methyl-3,4-diaza-tricyclo[6.2.1.0$^{2,7}$]undeca-2,4,6-triene light-yellow oil. MS (ESI): 297.1 ($MH^+$). Prepared from bicyclo[2.2.1]heptane-2,3-dione, (1,4,4-trimethyl-2-oxo-pentyl)-phosphonic acid diethyl ester, hydrazine monohydrate.

Example 6a,b (1S,8R)-5-(2,2-Dimethyl-propyl)-6-methyl-3,4-diaza-tricyclo[6.2.1.0$^{2,7}$]undeca-2,4,6-triene and (1R,8S)-5-(2,2-Dimethyl-propyl)-6-methyl-3,4-diaza-tricyclo[6.2.1.0$^{2,7}$]undeca-2,4,6-triene Submission of compound of example 6 to preparative HPLC, using a chiral column Chiralpak AD, with 5% isopropanol/heptane as eluant gave the two enantiomers, in optically pure form. Off-white solids.

Example 7

3-tert-Butyl-6,6-dimethyl-6,7-dihydro-5H-cyclopenta[c]pyridazine white crystalline solid. MS (ESI): 205.0 ($MH^+$). Prepared from 4,4-dimethyl-cyclopentane-1,2-dione, (3,3-dimethyl-2-oxo-butyl)-phosphonic acid dimethyl ester, hydrazine monohydrate.

Example 8

(1SR,8RS)-5-(3-Methyl-butyl)-3,4-diaza-tricyclo[6.2.1.0$^{2,7}$]undeca-2(7)3,5-triene yellow solid. MS (ESI): 217.4 ($MH^+$). Prepared from bicyclo[2.2.1]heptane-2,3-dione, (5-methyl-2-oxo-hexyl)-phosphonic acid dimethyl ester, hydrazine monohydrate.

Example 9

(1SR,8RS)-5-tert-Butyl-3,4-diaza-tricyclo[6.2.1.0$^{2,7}$]undeca-2,4,6-triene off-white crystalline solid. MS (EI): 245.2 ($M^+$). Prepared from bicyclo[2.2.1]heptane-2,3-dione, (3,3-dimethyl-2-oxo-butyl)-phosphonic acid dimethyl ester, hydrazine monohydrate.

Example 10

(1S,8R)-1,11,11-Trimethyl-5-(3-methyl-butyl)-3,4-diaza-tricyclo[6.2.1.0$^{2,7}$]undeca-2,4,6-triene yellow solid. MS (ESI): 259.0 ($MH^+$). Prepared from (1S,4R)-1,7,7-trimethyl-bicyclo[2.2.1]heptane-2,3-dione, (5-methyl-2-oxo-hexyl)-phosphonic acid dimethyl ester, hydrazine monohydrate.

Example 11

(1S,8R)-5-Isopropyl-1,11,11-trimethyl-3,4-diaza-tricyclo[6.2.1.0$^{2,7}$]undeca-2,4,6-triene off-white crystalline solid. MS (ESI): 231.0 ($MH^+$). Prepared from (1S,4R)-1,7,7-trimethyl-bicyclo[2.2.1]heptane-2,3-dione, (3-methyl-2-oxo-butyl)-phosphonic acid dimethyl ester, hydrazine monohydrate.

Example 12

(1SR,8RS)-5-Cyclopropylmethyl-3,4-diaza-tricyclo[6.2.1.0$^{2,7}$]undeca-2(7),3,5-triene light brow oil. MS (ESI): 201.1 ($MH^+$). Prepared from bicyclo[2.2.1]heptane-2,3-dione, (3-cyclopropyl-2-oxo-propyl)-phosphonic acid dimethyl ester, hydrazine monohydrate.

Example 13

(1S,8R)-5-Cyclopropylmethyl-1,11,11-trimethyl-3,4-diaza-tricyclo[6.2.1.0$^{2,7}$]undeca-2(7),3,5-triene Yellow solid. MS (ESI): 243.2 (MH$^+$). Prepared from (1S,4R)-1,7,7-trimethyl-bicyclo[2.2.1]heptane-2,3-dione, [(3-cyclopropyl-2-oxo-propyl)-phosphonic acid dimethyl ester, hydrazine monohydrate.

Example 14

3-Cyclopropylmethyl-6,6-dimethyl-6,7-dihydro-5H-cyclopenta[c]pyridazine

Prepared from 4,4-dimethyl-cyclopentane-1,2-dione, (3-cyclopropyl-2-oxo-propyl)-phosphonic acid dimethyl ester, hydrazine monohydrate.

Example 15

(1S,8R)-5-Cyclopentylmethyl-1,11,11-trimethyl-3,4-diaza-tricyclo[6.2.1.0$^{2,7}$]undeca-2,4,6-triene off-white crystalline solid. MS (ESI): 271.4 (MH$^+$). Prepared from (1S,4R)-1,7,7-trimethyl-bicyclo[2.2.1]heptane-2,3-dione, [(3-cyclopentyll-2-oxo-propyl)-phosphonic acid dimethyl ester, hydrazine monohydrate.

Example 16

(1S,8R)-5-(3,3-Dimethyl-butyl)-1,11,11-trimethyl-3,4-diaza-tricyclo[6.2.1.0$^{2,7}$]undeca-2,4,6-triene light yellow viscous oil MS (ESI): 273.2 (MH$^+$). Prepared from (1S,4R)-1,7,7-trimethyl-bicyclo[2.2.1]heptane-2,3-dione, (5,5-dimethyl-2-oxo-hexyl)-phosphonic acid dimethyl ester, hydrazine monohydrate.

Example 17

(1SR,8RS)-5-tert-Butyl-11,11-dimethyl-3,4-diaza-tricyclo[6.2.1.0$^{2,7}$]undeca-2.4.6-triene white solid MS (ESI): 231 (MH$^+$). Prepared from 7,7-dimethyl-bicyclo[2.2.1]heptane-2,3-dione (Childs, Ronald F.; Rogerson, Carol V.; J. Am. Chem. Soc.; EN; 102; 12; 1980; 4159), 3,3-dimethyl-2-oxo-butyl)-phosphonic acid dimethyl ester, hydrazine monohydrate.

Example 17a,b (1S,8R)-5-tert-Butyl-11,11-dimethyl-3,4-diaza-tricyclo[6.2.1.0$^{2,7}$]undeca-2,4,6-triene and (1R,8S)-5-tert-Butyl-11,11-dimethyl-3,4-diaza-tricyclo[6.2.1.0$^{2,7}$]undeca-2,4,6-triene Submission of compound of example 17 to preparative HPLC, using a chiral column Chiralpak AD, with 2% isopropanol/heptane as eluant gave the two enantiomers, in optically pure form. White solids.

Example 18

(1SR,8RS)-5-(2,2-Dimethyl-propyl)-11,11-dimethyl-3,4-diaza-tricyclo[6.2.1.0$^{2,7}$]undeca-2,4,6-triene light yellow solid. MS (ESI): 245.2 (MH$^+$). Prepared from 7,7-dimethyl-bicyclo[2.2.1]heptane-2,3-dione, (4,4-dimethyl-2-oxo-pentyl)-phosphonic acid dimethyl ester, hydrazine monohydrate.

Example 19

(1SR,8RS)-5-(2,2-Dimethyl-propyl)-6,11,11-trimethyl-3,4-diaza-tricyclo[6.2.1.0$^{2,7}$]undeca-2,4,6-triene yellow solid. MS (ESI): 259.3 (MH$^+$). Prepared from 7,7-dimethyl-bicyclo[2.2.1]heptane-2,3-dione, (1,4,4-trimethyl-2-oxo-pentyl)-phosphonic acid diethyl ester, hydrazine monohydrate.

Example 20

(1SR,8RS)-5-(1-Cyclopropyl-1-methyl-ethyl)-3,4-diaza-tricyclo[6.2.1.0$^{2,7}$]undeca-2,4,6-triene white solid. MS (ESI): 229.2 (MH$^+$). Prepared from bicyclo[2.2.1]heptan-2,3-dione, (3-cyclopropyl-3-methyl-2-oxo-butyl)-phosphonic acid dimethyl ester, hydrazine monohydrate. Submission of the racemate to preparative HPLC, using a chiral column, Chiralpak AD, with 5% isopropanol/heptane as eluant gave the two enantiomers, in optically pure form.

Example 21

(1SR,8RS)-5-Cyclopentylmethyl-3,4-diaza-tricyclo[6.2.1.0$^{2,7}$]undeca-2,4,6-triene light yellow gum. MS (ESI): 229.2 (MH$^+$). Prepared from bicyclo[2.2.1]heptan-2,3-dione, [(3-cyclopentyll-2-oxo-propyl)-phosphonic acid dimethyl ester, hydrazine monohydrate.

Example 22

(1R,8S)-5-(2,2-Dimethyl-propyl)-1,11,11-trimethyl-3,4-diaza-tricyclo[6.2.1.0$^{2,7}$]undeca-2(7),3,5-triene off-white solid. MS (ESI): 259.1 (MH$^+$). $^+$). Prepared from (1R,4S)-1,7,7-trimethyl-bicyclo [2.2.1]heptane-2,3-dione, (4,4-dimethyl-2-oxo-pentyl)-phosphonic acid dimethyl ester, hydrazine monohydrate. Main product, isolated and purified by silica gel chromatography.

Example 23

(1S,8R)-5-(2,2-Dimethyl-propyl)-8,11,11-trimethyl-3,4-diaza-tricyclo[6.2.1.0$^{2,7}$]undeca-2(7),3,5-triene white solid. MS (ESI): 259.1 (MH$^+$). Prepared from (1R,4S)-1,7,7-trimethyl-bicyclo[2.2.1]heptane-2,3-dione, (4,4-dimethyl-2-oxo-pentyl)-phosphonic acid dimethyl ester, hydrazine monohydrate. Minor product, regioisomer of compound of example 22, isolated and purified by silica gel chromatography.

Example 24

(1R,8S)-5-tert-Butyl-1,11,11-trimethyl-3,4-diaza-tricyclo[6.2.1.0$^{2,7}$]undeca-2(7),3,5-triene light yellow oil. MS (ESI): 245.2 (MH$^+$). Prepared from (1R,4S)-1,7,7-trimethyl-bicyclo[2.2.1]heptane-2,3-dione, (3,3-dimethyl-2-oxo-butyl)-phosphonic acid dimethyl ester, hydrazine monohydrate. Main product isolated and purified by silica gel chromatography.

Example 25

(1S,8R)-5-tert-Butyl-8,11,11-trimethyl-3,4-diaza-tricyclo[6.2.1.0$^{2,7}$]undeca-2(7),3,5-triene light yellow oil. MS (ESI): 245.2 (MH$^+$). Prepared from (1R,4S)-1,7,7-trimethyl-bicyclo[2.2.1]heptane-2,3-dione, (3,3-dimethyl-2-oxo-butyl)-phosphonic acid dimethyl ester, hydrazine monohydrate. Minor product, regioisomer of compound of example 24, isolated and purified by silica gel chromatography.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims.

What is claimed is:

1. A compound of formula (I):

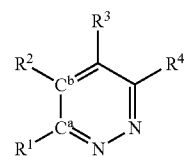

wherein

R$^1$ is cycloalkyl, arylalkyl or aryloxyalkyl;
R$^1$ is cycloalkyl, arylalkyl or aryloxyalkyl; or
R$^1$ and R$^2$ together with the carbon atoms C$^a$ and C$^b$ to which they are attached form

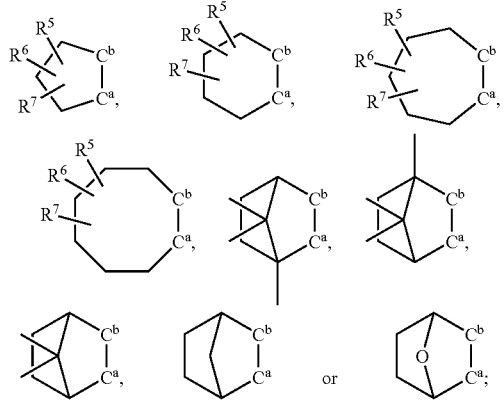

R$^3$ is hydrogen, alkyl, cycloalkyl or trifluoromethyl;
R$^4$ is 2,2-dimethyl-propyl, 3-methyl-butyl, iso-propyl, tert-butyl, cyclopropylmethyl, cyclopentylmethyl, 3,3-dimethyl-butyl or 1-cyclopropyl-1-methyl-ethyl;
R$^5$ is hydrogen, alkyl cycloalkyl or alkoxy;
R$^6$ is hydrogen, alkyl, cycloalkyl or alkoxy;
R$^7$ is hydrogen, alkyl, cycloalkyl or alkoxy;
and pharmaceutically acceptable salts thereof.

2. The compound according to claim 1, wherein R$^4$ is 2,2-dimethyl-propyl, 3-methyl-butyl, iso-propyl, tert-butyl, cyclopropylmethyl or cyclopentylmethyl.

3. The compound according to claim 1, wherein R$^1$ and R$^2$ together with the carbon atoms C$^a$ and C$^b$ to which they are attached form

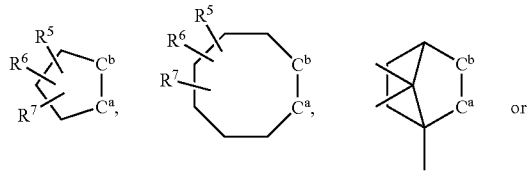

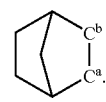

4. The compound according to claim 1, wherein $R^1$ and $R^2$ together with the carbon atoms $C^a$ and $C^b$ to which they are attached form

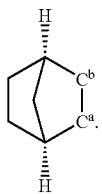

5. The compound according to claim 1, wherein $R^1$ and $R^2$ together with the carbon atoms $C^a$ and $C^b$ to which they are attached form

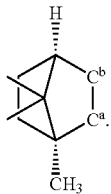

6. The compound according to claim 1, wherein $R^1$ and $R^2$ together with the carbon atoms $C^a$ and $C^b$ to which they are attached form

7. The compound according to claim 1, wherein $R^1$ and $R^2$ together with the carbon atoms $C^a$ and $C^b$ to which they are attached form

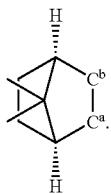

8. The compound according to claim 1, wherein $R^3$ is hydrogen.

9. The compound according to claim 1, wherein $R^3$ is methyl.

10. The compound according to claim 1, wherein $R^4$ is 2,2-dimethyl-propyl or tert-butyl.

11. The compound according to claim 1, wherein $R^4$ is 3-methyl-butyl.

12. The compound according to claim 1, wherein $R^5$, $R^6$ and $R^7$ are independently selected from hydrogen and methyl.

13. The compound according to claim 1, wherein $R^5$, $R^6$ and $R^7$ are hydrogen.

14. The compound according to claim 1, selected from 3-(2,2-Dimethyl-propyl)-5,6,7,8,9,10-hexahydro-cycloocta[c]pyridazine;

(1SR,8RS)-5-(2,2-Dimethyl-propyl)-3,4-diaza-tricyclo[6.2.1.0$^{2,7}$]undeca-2,4,6-triene;
(1S,8R)-5-(2,2-Dimethyl-propyl)-1,11,11-trimethyl-3,4-diaza-tricyclo[6.2.1.0$^{2,7}$]undeca-2,4,6-triene;
(1S,8R)-5-tert-Butyl-1,11,11-trimethyl-3,4-diaza-tricyclo[6.2.1.0$^{2,7}$]undeca-2,4,6-triene;
3-(2,2-Dimethyl-propyl)-6,6-dimethyl-6,7-dihydro-5H-cyclopenta[c]pyridazine;
(1SR,8RS)-5-(2,2-Dimethyl-propyl)-6-methyl-3,4-diaza-tricyclo[6.2.1.0$^{2,7}$]undeca-2,4,6-triene;
3-tert-Butyl-6,6-dimethyl-6,7-dihydro-5H-cyclopenta[c]pyridazine;
(1SR,8RS)-5-(3-Methyl-butyl)-3,4-diaza-tricyclo[6.2.1.0$^{2,7}$]undeca-2(7),3,5-triene;
(1SR,8RS)-5-tert-Butyl-3,4-diaza-tricyclo[6.2.1.0$^{2,7}$]undeca-2,4,6-triene;
(1S,8R)-1,11,11-Trimethyl-5-(3-methyl-butyl)-3,4-diaza-tricyclo[6.2.1.0$^{2,7}$]undeca-2,4,6,-triene;
(1S,8R)-5-Isopropyl-1,11,11-trimethyl-3,4-diaza-tricyclo[6.2.1.0$^{2,7}$]undeca-2,4,6-triene;
(1SR,8RS)-5-Cyclopropylmethyl-3,4-diaza-tricyclo[6.2.1.0$^{2,7}$]undeca-2(7),3,5-triene;
(1S,8R)-5-Cyclopropylmethyl-1,11,11-trimethyl-3,4-diaza-tricyclo[6.2.1.0$^{2,7}$]undeca-2(7),3,5-triene;
3-Cyclopropylmethyl-6,6-dimethyl-6,7-dihydro-5H-cyclopenta[c]pyridazine; and
(1S,8R)-5-Cyclopentylmethyl-1,11,11-trimethyl-3,4-diaza-tricyclo[6.2.1.0$^{2,7}$]undeca-2,4,6-triene.

15. The compound according to claim 1, selected from
(1SR,8RS)-5-(2,2-Dimethyl-propyl)-3,4-diaza-tricyclo[6.2.1.0$^{2,7}$]undeca-2,4,6-triene;
(1S,8R)-5-(2,2-Dimethyl-propyl)-1,11,11-trimethyl-3,4-diaza-tricyclo[6.2.1.0$^{2,7}$]undeca-2,4,6-triene;
(1S,8R)-5-tert-Butyl-1,11,11-trimethyl-3,4-diaza-tricyclo[6.2.1.0$^{2,7}$]undeca-2,4,6-triene;
(1SR,8RS)-5-(2,2-Dimethyl-propyl)-6-methyl-3,4-diaza-tricyclo[6.2.1.0$^{2,7}$]undeca-2,4,6-triene;
3-tert-Butyl-6,6-dimethyl-6,7-dihydro-5H-cyclopenta[c]pyridazine; and
(1S,8R)-1,11,11-Trimethyl-5-(3-methyl-butyl)-3,4-diaza-tricyclo[6.2.1.0$^{2,7}$]undeca-2,4,6-triene.

16. The compound according to claim 1, selected from
(1S,8R)-5-(2,2-Dimethyl-propyl)-6-methyl-3,4-diaza-tricyclo[6.2.1.0$^{2,7}$]undeca-2,4,6-triene;
(1S,8R)-5-(2,2-Dimethyl-propyl)-6-methyl-3,4-diaza-tricyclo[6.2.1.0$^{2,7}$]undeca-2,4,6-triene;
(1S,8R)-5-(3,3-Dimethyl-butyl)-1,11,11-trimethyl-3,4-diaza-tricyclo[6.2.1.0$^{2,7}$]undeca-2,4,6-triene;
(1SR,8RS)-5-tert-Butyl-11,11-dimethyl-3,4-diaza-tricyclo[6.2.1.0$^{2,7}$]undeca-2,4,6-triene;
(1S,8R)-5-tert-Butyl-11,11-dimethyl-3,4-diaza-tricyclo[6.2.1.0$^{2,7}$]undeca-2,4,6-triene;
(1R,8S)-5-tert-Butyl-11,11-dimethyl-3,4-diaza-tricyclo[6.2.1.0$^{2,7}$]undeca-2,4,6-triene;
(1SR,8RS)-5-(2,2-Dimethyl-propyl)-11,11-dimethyl-3,4-diaza-tricyclo[6.2.1.0$^{2,7}$]undeca-2,4,6-triene;
(1SR,8RS)-5-(2,2-Dimethyl-propyl)-6,11,11-trimethyl-3,4-diaza-tricyclo[6.2.1.0$^{2,7}$]undeca-2,4,6-triene;
(1SR,8RS)-5-(1-Cyclopropyl-1-methyl-ethyl)-3,4-diaza-tricyclo[6.2.1.0$^{2,7}$]undeca-2,4,6-triene;
(1SR,8RS)-5-Cyclopentylmethyl-3,4-diaza-tricyclo[6.2.1.0$^{2,7}$]undeca-2,4,6-triene;
(1R,8S)-5-(2,2-Dimethyl-propyl)-1,11,11-trimethyl-3,4-diaza-tricyclo[6.2.1.0$^{2,7}$]undeca -2(7),3,5-triene;
(1S,8R)-5-(2,2-Dimethyl-propyl)-8,11,11-trimethyl-3,4-diaza-tricyclo[6.2.1.0$^{2,7}$]undeca -2(7),3,5-triene;

(1R,8S)-5-tert-Butyl-1,11,11-trimethyl-3,4-diaza-tricyclo[6.2.1 0$^{2,7}$]undeca-2(7),3,5-triene; and
(1S,8R)-5-tert-Butyl-8,11,11-trimethyl-3,4-diaza-tricyclo[6.2.1.0$^{2,7}$]undeca-2(7),3,5-triene.

17. The compound according to claim 1, selected from
(1S,8R)-5-(2,2-Dimethyl-propyl)-6-methyl-3,4-diaza-tricyclo[6.2.1.0$^{2,7}$]undeca-2,4,6-triene;
(1S,8R)-5-(2,2-Dimethyl-propyl)-6-methyl-3,4-diaza-tricyclo[6.2.1.0$^{2,7}$]undeca-2,4,6-triene;
(1S,8R)-5-tert-Butyl-11,11-dimethyl-3,4-diaza-tricyclo[6.2.1.0$^{2,7}$]undeca-2,4,6-triene;
(1R,8S)-5-tert-Butyl-11,11-dimethyl-3,4-diaza-tricyclo[6.2.1.0$^{2,7}$]undeca-2,4,6-triene;
(1SR,8RS)-5-(2,2-Dimethyl-propyl)-11,11-dimethyl-3,4-diaza-tricyclo[6.2.1.0$^{2,7}$]undeca -2,4,6-triene;
(1S,8R)-5-(2,2-Dimethyl-propyl)-8,11,11-trimethyl-3,4-diaza-tricyclo[6.2.1$^{2,7}$]undeca-2(7),3,5-triene; and
(1S,8R)-5-tert-Butyl-8,11,11-trimethyl-3,4-diaza-tricyclo[6.2.1.0$^{2,7}$]undeca-2(7),3,5-triene.

18. A process for the preparation of a compound according to claim 1, comprising the of the step of reacting a compound according to formula (II)

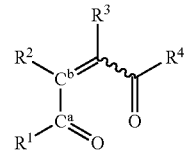

(II)

with hydrazine; wherein R$^1$ to R$^4$ are defined as in claim 1.

19. A pharmaceutical composition, comprising a therapeutically effective amount of a compound according to claim 1 and a therapeutically inert carrier.

* * * * *

UNITED STATES PATENT AND TRADEMARK OFFICE
CERTIFICATE OF CORRECTION

PATENT NO. : 7,547,697 B2  
APPLICATION NO. : 11/824971  
DATED : June 16, 2009  
INVENTOR(S) : Kurt Amrein et al.

It is certified that error appears in the above-identified patent and that said Letters Patent is hereby corrected as shown below:

Column 16, line 15, please delete: "R1 is cycloalkyl, arylalkyl or aryloxyalkyl; or" and insert: --R2 is cycloalkyl, arylalkyl or aryloxyalkyl; or--

Signed and Sealed this

Eleventh Day of August, 2009

David J. Kappos
*Director of the United States Patent and Trademark Office*